(12) United States Patent
Shelokov

(10) Patent No.: US 8,114,159 B2
(45) Date of Patent: Feb. 14, 2012

(54) ANTERIOR SPINAL VESSEL PROTECTOR

(75) Inventor: Alexis P. Shelokov, Dallas, TX (US)

(73) Assignee: DePuy Spine, Inc., Raynham, MA (US)

( * ) Notice: Subject to any disclaimer, the term of this patent is extended or adjusted under 35 U.S.C. 154(b) by 1233 days.

(21) Appl. No.: 11/601,900

(22) Filed: Nov. 20, 2006

(65) Prior Publication Data

US 2008/0119851 A1    May 22, 2008

(51) Int. Cl.
*A61F 5/37* (2006.01)
*A61F 13/00* (2006.01)
*A61F 2/30* (2006.01)
*A61F 2/28* (2006.01)
*A61F 2/44* (2006.01)
*A61B 17/56* (2006.01)
*A61B 17/58* (2006.01)
*A61B 17/08* (2006.01)

(52) U.S. Cl. ............ 623/17.12; 128/846; 128/888; 606/60; 606/88; 606/99; 606/151; 623/16.11; 623/17.11

(58) Field of Classification Search .............. 128/846, 128/888; 606/99, 151, 60; 623/17.12
See application file for complete search history.

(56) References Cited

U.S. PATENT DOCUMENTS

| | | |
|---|---|---|
| 3,328,259 A | 6/1967 | Anderson |
| 3,387,061 A | 6/1968 | Smith et al. |
| 3,640,741 A | 2/1972 | Etes |
| 4,013,078 A | 3/1977 | Feild |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,181,983 A | 1/1980 | Kulkarni |
| 4,205,399 A | 6/1980 | Shalaby et al. |
| 4,208,511 A | 6/1980 | Shalaby et al. |
| 4,292,972 A | 10/1981 | Pawelchak et al. |
| 4,554,156 A | 11/1985 | Fischer et al. |
| 4,717,713 A | 1/1988 | Zatz et al. |
| 4,767,751 A | 8/1988 | Davis |
| 4,769,038 A * | 9/1988 | Bendavid et al. ......... 623/13.11 |
| 4,826,945 A | 5/1989 | Cohn et al. |
| 4,946,870 A | 8/1990 | Partain, III. et al. |
| 4,973,473 A | 11/1990 | Schneider et al. |
| 4,983,585 A | 1/1991 | Pennell et al. |
| 5,017,229 A | 5/1991 | Burns et al. |
| 5,071,823 A | 12/1991 | Matsushita et al. |
| 5,080,893 A | 1/1992 | Goldberg et al. |
| 5,156,839 A | 10/1992 | Pennell et al. |
| 5,415,661 A | 5/1995 | Holmes |

(Continued)

OTHER PUBLICATIONS

Harry R. Allcock, Polyphosphazenes, The Encyclopedia of Polymer Science, 1988, pp. 31-41, vol. 13, Wiley Intersciences, John Wiley & Sons. (11 pages).

(Continued)

*Primary Examiner* — Patricia M Bianco
*Assistant Examiner* — Brandon Jackson
(74) *Attorney, Agent, or Firm* — Maginot, Moore & Beck

(57) ABSTRACT

A protective system for facilitating revision surgery includes a protective pad with a base portion and an overlying portion spaced apart from the base. A fluid pocket is formed between the base portion and the overlying portion. The protective system prevents formation of adhesions or scar tissue in the area occupied by the protective pad. Thus a clean plane is obtained during revision surgery on the patient through an incision in the fluid pocket.

9 Claims, 8 Drawing Sheets

U.S. PATENT DOCUMENTS

| | | | |
|---|---|---|---|
| 5,437,672 A | 8/1995 | Alleyne | |
| 5,464,929 A | 11/1995 | Bezwada et al. | |
| 5,532,221 A | 7/1996 | Huang et al. | |
| 5,591,169 A | 1/1997 | Benoist | |
| 5,593,441 A | 1/1997 | Lichtenstein et al. | |
| 5,595,751 A | 1/1997 | Bezwada et al. | |
| 5,597,579 A | 1/1997 | Bezwada et al. | |
| 5,607,687 A | 3/1997 | Bezwada et al. | |
| 5,611,354 A | 3/1997 | Alleyne | |
| 5,618,552 A | 4/1997 | Bezwada et al. | |
| 5,620,698 A | 4/1997 | Bezwada et al. | |
| 5,645,599 A | 7/1997 | Samani | |
| 5,645,850 A | 7/1997 | Bezwada et al. | |
| 5,648,088 A | 7/1997 | Bezwada et al. | |
| 5,681,310 A | 10/1997 | Yuan et al. | |
| 5,697,978 A * | 12/1997 | Sgro | 623/23.64 |
| 5,698,213 A | 12/1997 | Jamiolkowski et al. | |
| 5,700,583 A | 12/1997 | Jamiolkowski et al. | |
| 5,792,128 A | 8/1998 | DeBusk | |
| 5,859,150 A | 1/1999 | Jamiolkowski et al. | |
| 5,868,745 A | 2/1999 | Alleyne | |
| 5,891,824 A | 4/1999 | Simpson et al. | |
| 5,906,997 A | 5/1999 | Schwartz et al. | |
| 6,017,301 A | 1/2000 | Schwartz et al. | |
| 6,034,140 A | 3/2000 | Schwartz et al. | |
| 6,039,763 A | 3/2000 | Shelokov | |
| 6,133,325 A | 10/2000 | Schwartz et al. | |
| 6,179,840 B1 | 1/2001 | Bowman | |
| 6,206,882 B1 | 3/2001 | Cohen | |
| 6,364,884 B1 | 4/2002 | Bowman et al. | |
| 6,402,766 B2 | 6/2002 | Bowman et al. | |
| 6,423,073 B2 | 7/2002 | Bowman | |
| 6,436,110 B2 | 8/2002 | Bowman et al. | |
| 6,468,928 B2 | 10/2002 | Eysel et al. | |
| 6,475,219 B1 * | 11/2002 | Shelokov | 606/281 |
| 6,482,491 B1 | 11/2002 | Samuelsen et al. | |
| 6,497,707 B1 | 12/2002 | Bowman et al. | |
| 6,569,938 B1 | 5/2003 | Puett | |
| 6,652,585 B2 | 11/2003 | Lange | |
| 6,869,938 B1 | 3/2005 | Schwartz et al. | |
| 7,553,325 B2 * | 6/2009 | Stinson | 623/1.34 |
| 7,758,654 B2 | 7/2010 | Hoganson | |
| 2002/0052628 A1 | 5/2002 | Bowman | |
| 2002/0095157 A1 | 7/2002 | Bowman | |
| 2002/0095205 A1 | 7/2002 | Edwin et al. | |
| 2002/0120270 A1 | 8/2002 | Trieu et al. | |
| 2002/0169465 A1 | 11/2002 | Bowman et al. | |
| 2003/0078588 A1 | 4/2003 | Alleyne | |
| 2004/0018228 A1 | 1/2004 | Fischell et al. | |
| 2004/0138664 A1 | 7/2004 | Bowman | |
| 2004/0230309 A1 * | 11/2004 | DiMauro et al. | 623/17.12 |
| 2005/0126576 A1 | 6/2005 | Ferree | |
| 2005/0165485 A1 * | 7/2005 | Trieu | 623/17.13 |
| 2005/0192600 A1 | 9/2005 | Nicolo et al. | |
| 2005/0192699 A1 | 9/2005 | Lin et al. | |
| 2005/0228491 A1 | 10/2005 | Snyder et al. | |
| 2007/0297987 A1 | 12/2007 | Stad et al. | |

OTHER PUBLICATIONS

Jorge Heller, Poly(ortho esters), Handbook of Biodegradable Polymers, edited by Domb, et al., 1997, pp. 99-118, Hardwood Academic Press. (20 pages).

Daniel Cohn and Hani Younes, Biodegradable PEO/PLA Block Copolymers, Journal of Biomaterials Research, 1988, pp. 993-1009, vol. 22. (17 pages).

John Kemnitzer and Joachim Kohn, Degradable Polymers Derived from the Amino Acid L-Tyrosine, Handbook of Biodegradable Polymers, edited by Domb, et. al., 1997, pp. 251-272, Hardwood Academic Press. (22 pages).

D. Cohn, Polymer Preprints (ACS Division of Polymer Chemistry), Papers Presented at the Dallas, Texas Meeting, Apr. 1989, p. 498, vol. 30(1). (2 pages).

J. Vandorpe, et al., Biodegradable Polyphosphazenes for Biomedical Applications, Handbook of Biodegradable Polymers, edited by Domb, et al., 1997, pp. 161-182, Hardwood Academic Press. (22 pages).

* cited by examiner

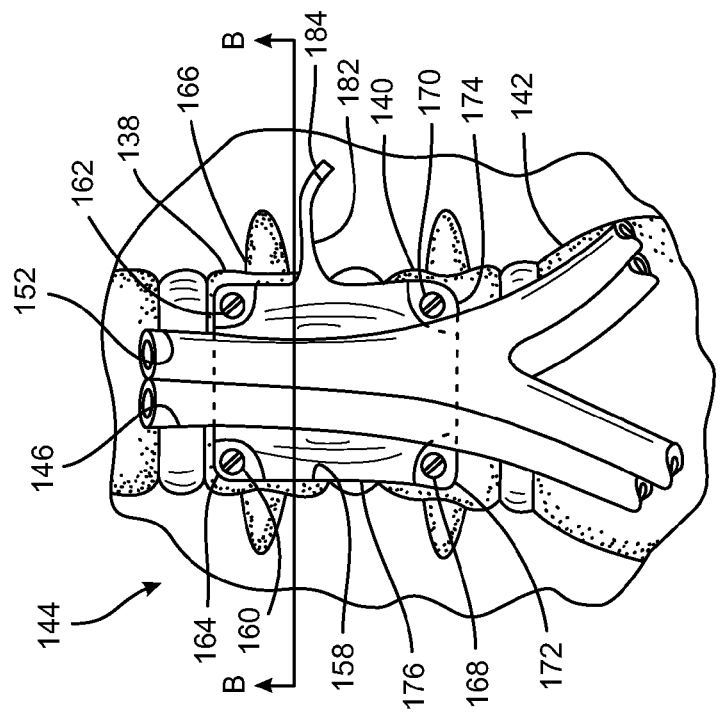
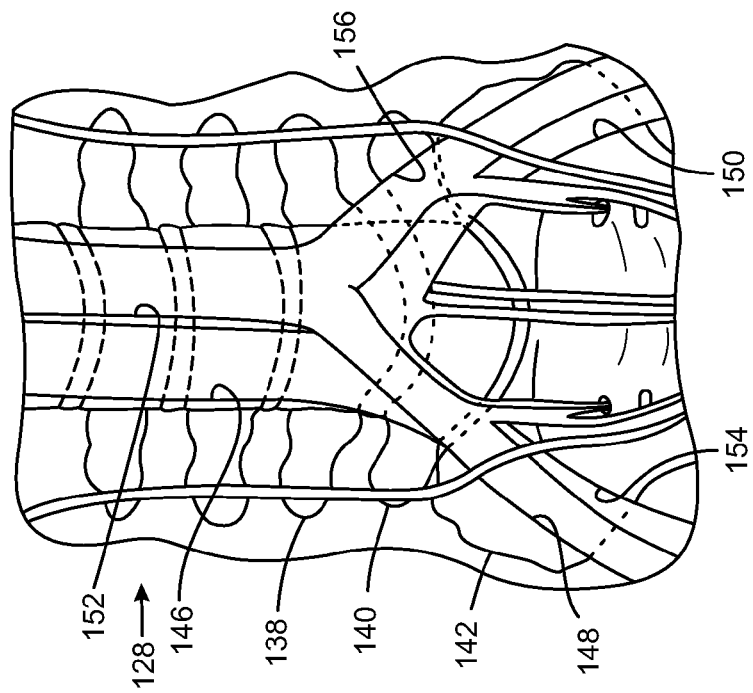

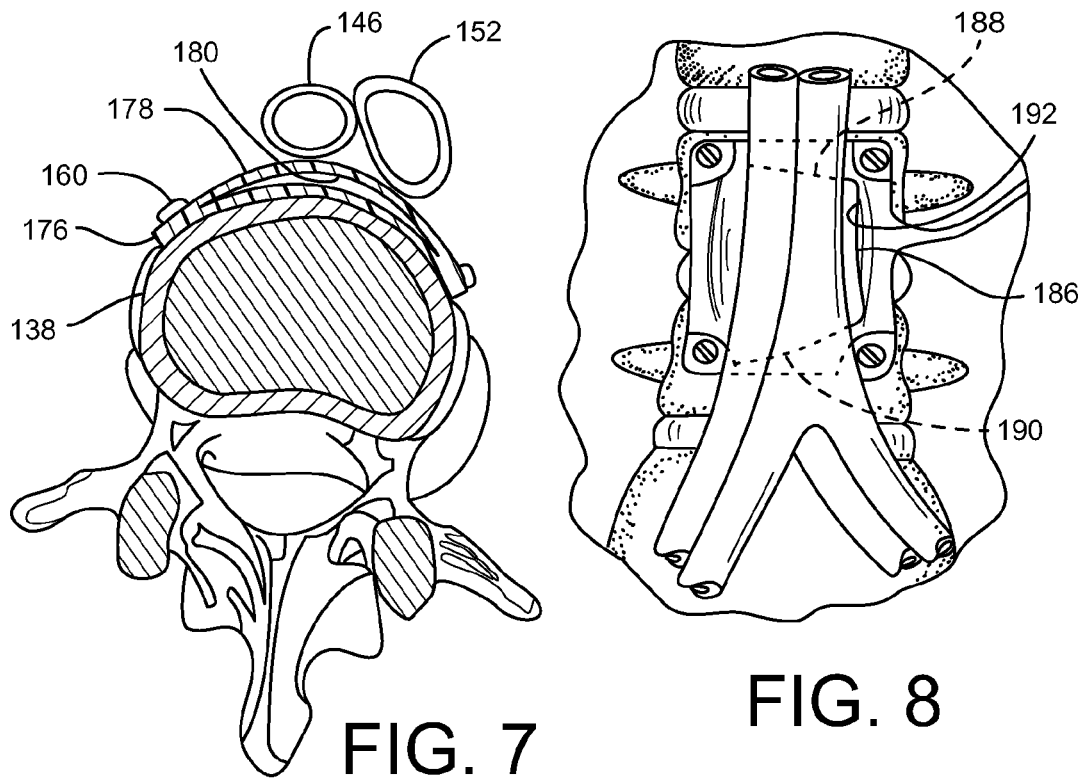
FIG. 7
FIG. 8
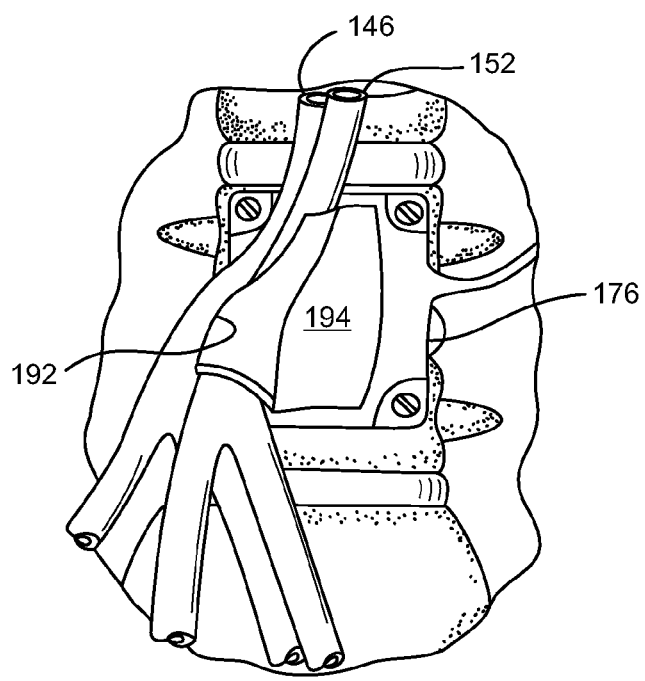
FIG. 9

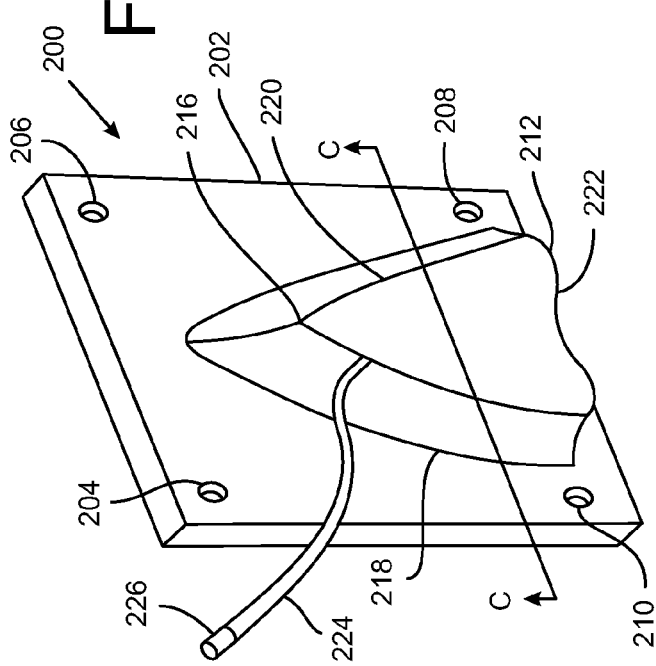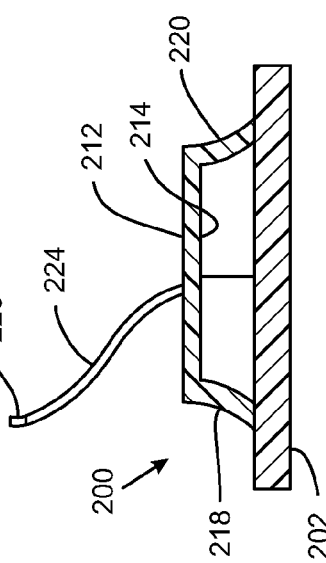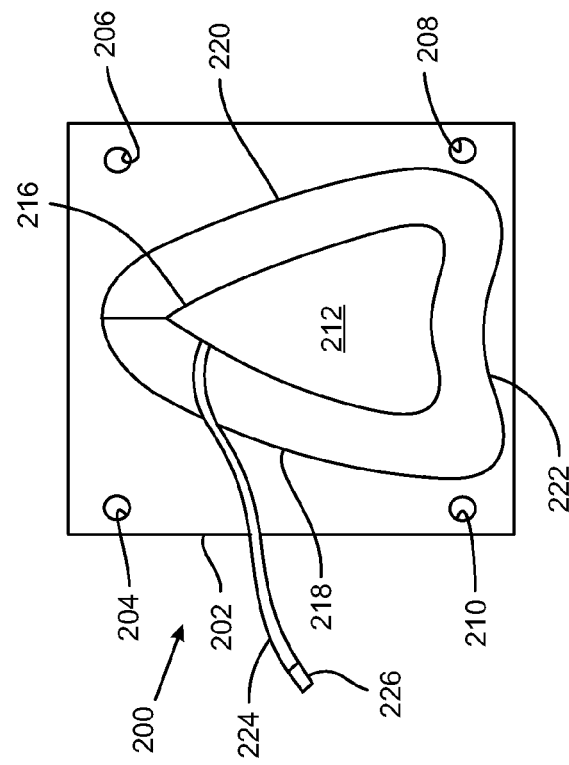

ANTERIOR SPINAL VESSEL PROTECTOR

FIELD OF THE INVENTION

This invention relates to surgical devices and, more particularly, to devices used to facilitate revision surgery implicating vulnerable anatomical parts.

BACKGROUND

Spinal disorders requiring surgical procedures are well known. The lumbar region of the human anatomy, for example, is a frequent site of spinal disorders which may be corrected by surgical procedures carried out anteriorly of the lumbar vertebrae including, for example, surgical procedures involving disc removal and/or replacement.

In anterior spinal surgical procedures, the initial surgery is through an unscarred and substantially clear path to the surgical site. In revision surgery, however, the path to the surgical site has typically degraded as a result of the previous surgery resulting in scarring and other developments which may interfere with the revision surgery.

Moreover, the present technology in spinal surgeries is typically focused on anterior insertion of intervertebral prostheses, and other anterior surgical procedures. Consequently, the potential of anterior dislocation of prostheses and vertebral structures as well as potential injury to the significant blood vessels located in proximity to the spine is increased.

U.S. Pat. No. 6,475,219 issued to Alexis P. Shelekov on Nov. 5, 2002, addressed the aforementioned conditions. The '219 patent, the teachings of which are herein incorporated by reference, discloses a method and device for protecting major vessels and other anatomical parts from complications as a consequence of anterior spinal surgical procedures. In particular, the '219 patent discloses a method for protecting major blood vessels, such as the aorta and the vena cava, and providing some protection against anterior dislocation of vertebral bodies adjacent these vessels. The '219 patent also provides for minimizing the formation of adhesions or unwanted joining of certain tissues and body structures to each other pursuant to anterior spinal surgery.

The '219 patent provides a significant improvement in protection of vulnerable anatomical parts in areas subject to revision surgery. Nonetheless, a need exists for a device which further simplifies revision surgeries, particularly in the area of vulnerable body parts. It would be advantageous if the device facilitated location of the targeted surgical area. Moreover, it would be beneficial if the device could be conveniently interposed between the spinal column and anatomical parts, particularly, major blood vessels such as the aorta and the vena cava, so that the anatomical parts are protected during a surgical procedure and/or are not subject to the development of adhesions or tissue which may produce complications during revision surgery.

SUMMARY

A protective system and method is disclosed. In accordance with one method according to the invention, a patient is prepared for a first surgical procedure. A first incision is made through the skin of the patient in accordance with the first surgical procedure and a target area for the first surgical procedure is exposed through the first incision. A step of the first surgical procedure is then performed on the target area for the first surgical procedure. Thereafter, a protective pad with a fluid pocket is placed between a vulnerable anatomical part and the target area for the first surgical procedure and the first incision is closed in accordance with the first surgical procedure with the protective pad between the vulnerable anatomical part and the target area.

In one embodiment, a protective system for facilitating revision surgery includes a protective pad with a base portion of biocompatible material and an overlying portion of biocompatible material spaced apart from the base, the base portion and the overlying portion forming at least a portion of a fluid pocket. The system further includes at least one bone anchor for affixing the protective pad to a bone.

The above-described features and advantages, as well as others, will become more readily apparent to those of ordinary skill in the art by reference to the following detailed description and accompanying drawings.

BRIEF DESCRIPTION OF THE DRAWINGS

FIG. 5 shows a partial schematic view of a portion of the prevertebral space of FIG. 4 superimposed upon a portion of the spinal column of FIG. 3 to illustrate the location of some of the anatomical parts of FIG. 4 relative to the spinal column;

FIG. 6 shows a partial anterior perspective view of a protective pad attached to the spinal column of FIG. 3 underneath the aorta and the vena cava of a patient;

FIG. 7 shows a cross-sectional view of the protective pad of FIG. 6 taken along the line B-B of FIG. 6 wherein the fluid pocket of the protective pad is located between the spinal column and the aorta and the vena cava of the patient;

FIG. 8 shows a partial anterior perspective view of the protective pad of FIG. 6 with incisions made therein to form a leaf;

FIG. 9 shows a partial anterior perspective view of the protective pad of FIG. 6 with the leaf retracted so as to retract the aorta and the vena cava of the patient and to expose a portion of the base of the protective pad;

FIG. 10 shows a perspective view of an alternative protective pad with a telltale made in accordance with principles of the present invention that separates vulnerable anatomical parts from a target area of a spine and further extends between the vulnerable anatomical parts to facilitate access to a target area through the space between the anatomical parts;

FIG. 11 shows a cross-sectional view of the protective pad of FIG. 10 taken along the line C-C of FIG. 10 showing concave trailing portions extending away from the front end of the protective pad;

FIG. 12 shows a top plan view of the protective pad of FIG. 10;

DETAILED DESCRIPTION

Figure 1:
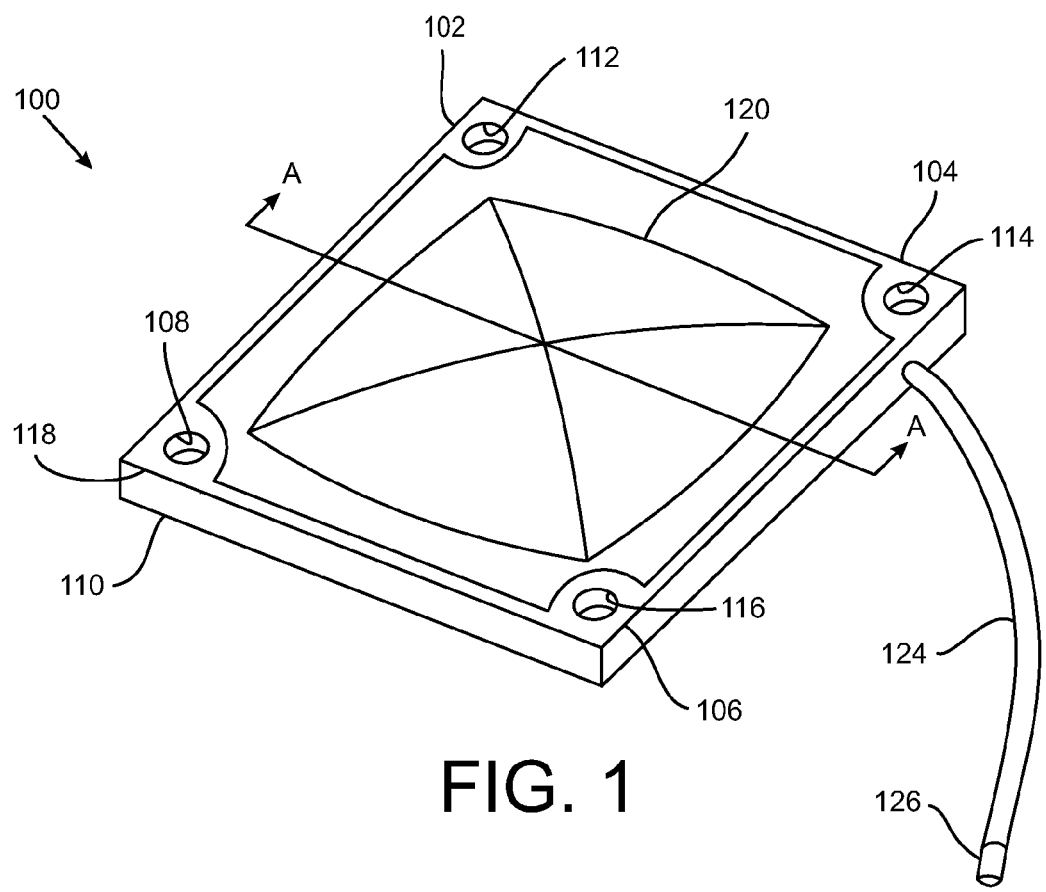
FIG. 1 shows a perspective view of a protective pad with a telltale made in accordance with principles of the present invention.

FIG. 1 depicts a protective pad 100. The protective pad 100 has a generally rectangular shape with four fastener areas 102, 104, 106 and 108 located at each of the four corners of a base 110 of the protective pad 100. In this embodiment, the fastener areas 102, 104, 106 and 108 include bone fastener holes 112, 114, 116 and 118. The bone fastener holes 112, 114, 116 and 118 may be used with a bone fastener such as a screw, peg or nail to attach the protective pad 100 to a bone. Alternatively, the protective pad 100 may be sutured in place.

Figure 2:
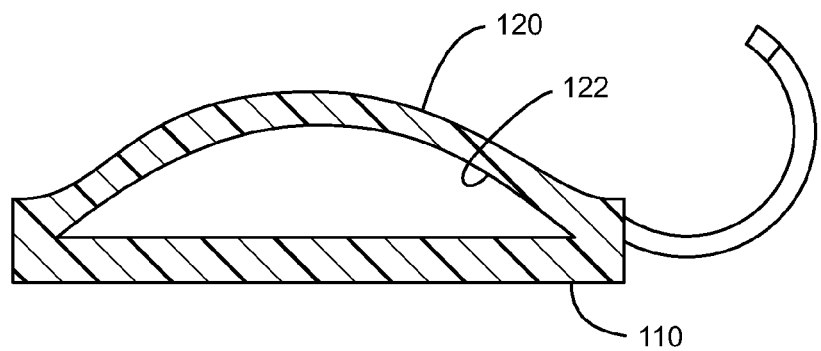
FIG. 2 shows a cross-sectional view of the protective pad of FIG. 1 taken along the line A-A of FIG. 1.

As shown in FIG. 2, an overlying portion 120 extends above a portion of the base 110. The overlying portion 120 and the base 110 define a fluid pocket 122. In the embodiment of FIG. 2, the overlying portion 120 and the base 110 are configured to provide an impermeable barrier about the fluid pocket 122. Accordingly, fluid within the fluid pocket 122 is not allowed to exit the fluid pocket 122. Additionally, fluids outside of the protective pad 100 are not allowed to enter the fluid pocket 122. The protective pad 100 further includes a telltale 124 which in this embodiment extends from the base 110. The telltale 124 includes a marker 126.

The overlying portion 120, the base 110 and the telltale 124 are formed from a flexible biocompatible material or subdermal implant material, such as Silastic brand silicone rubber or similar organosiloxane polymers. The fluid pocket 122 is filled with a biocompatible fluid which may be liquid or gaseous. In one embodiment, carbon dioxide gas is used. Other biologically inert gasses may be used in alternative embodiments. The fluid pocket 122 may be configured to provide a thin layer of fluid between the overlying portion 120 and the base 110 or to provide a more substantial separation between the overlying portion 120 and the base 110 as shown in FIG. 2. The marker 126 in the embodiment of FIG. 1 includes a radiodense material so as to be readily identified using radiography.

Figure 3:
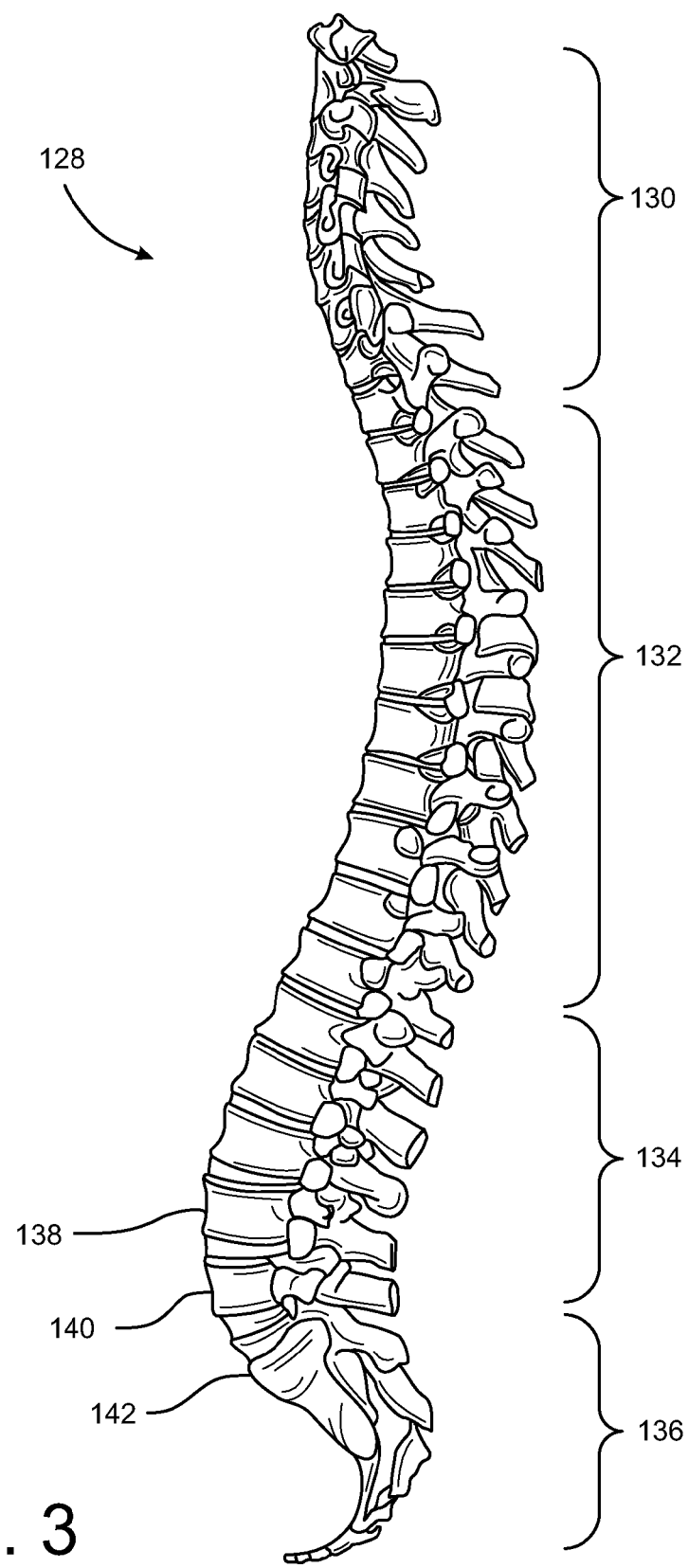
FIG. 3 shows a side perspective view of a spinal column upon which the protective pad of FIG. 1 may be placed in accordance with principles of the present invention.

The present invention is particularly well suited for use in surgeries on the spinal column of a patient. Referring to FIG. 3, a spinal column 128 of a human being is illustrated. In the drawing figures, certain anatomical details may be omitted or shown somewhat schematically in the interest of clarity. The spinal column 128 includes a cervical region 130, a dorsal region 132, a lumbar region 134 and a pelvic region 136.

Two of the regions of the spinal column 128 that are most commonly operated on are the lumbar region 134 and the pelvic region 136. In these regions, the area including lumbar L4 138 and lumbar L5 140 and the area including lumbar L5 140 and the sacrum 142 are the areas to which most spinal operations are directed.

One surgical approach that is used when performing a surgical procedure on the above described areas is identified as the Pararectal Retroperitoneal Approach. In this approach, which may be used for procedures such as a disc removal or disc prosthesis installation, the skin of the patient is incised in a curved line over the lateral border of the rectus muscle of the patient. Through this incision, the prevertebral space of the patient is exposed.

Figure 4:
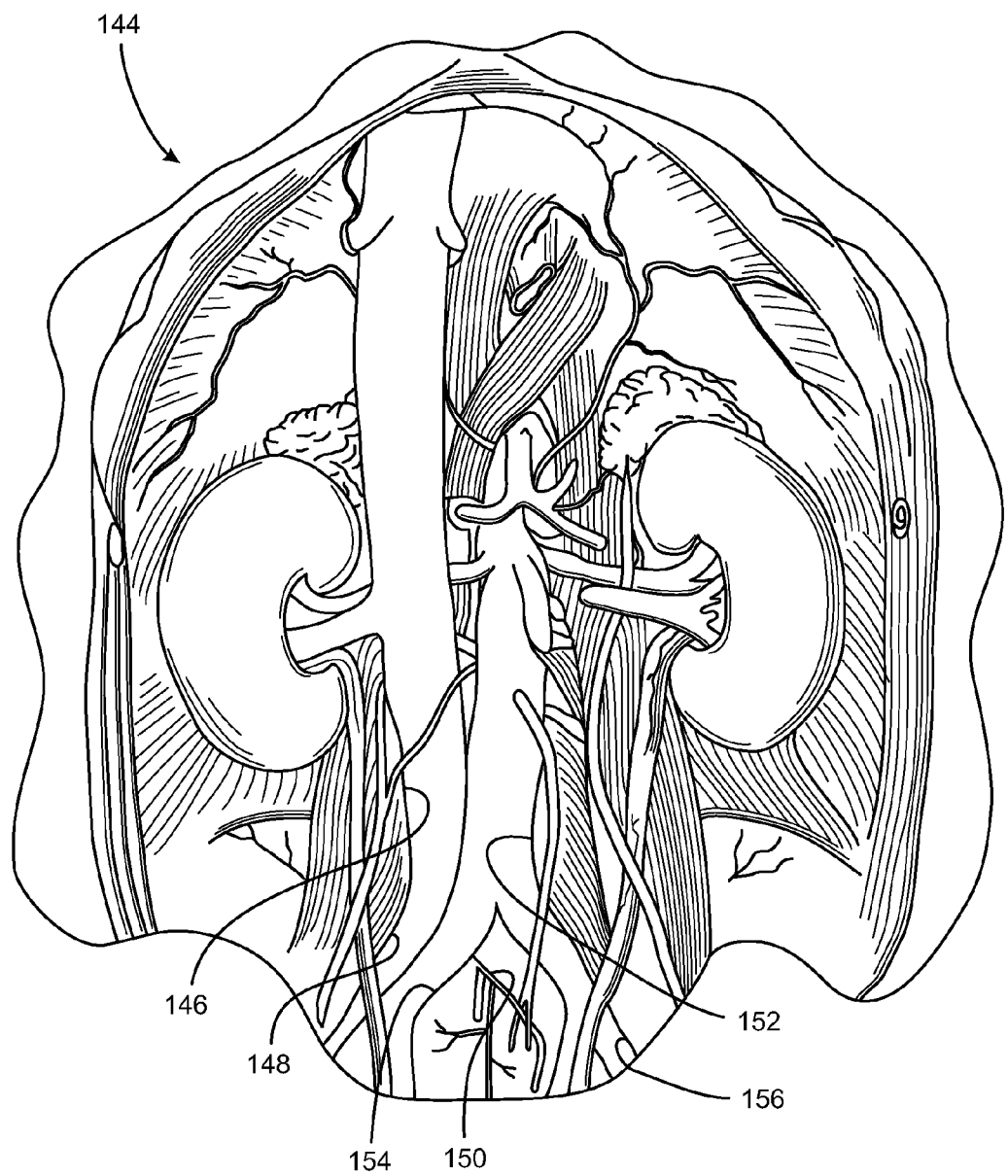
FIG. 4 shows a partial perspective anterior view of a prevertebral space including anatomical parts which may be encountered during a surgical procedure in accordance with principles of the present invention.

FIG. 4 depicts various anatomical parts that are located within or adjacent to a prevertebral space 144. As depicted therein, the vena cava 146 extends generally along a line directly above the spinal column (not shown in FIG. 4). The vena cava 146 receives blood from the common iliac veins 148 and 150 and their respective branches. The abdominal aorta 152 begins to the right of the vena cava 146 as viewed in FIG. 4 and extends over the top of the vena cava 146 lower down in the prevertebral space 144. The abdominal aorta 152 provides blood to two common iliac arteries 154 and 156 and their respective branches.

The vena cava 146, the common iliac veins 148 and 150 and their respective branches, the abdominal aorta 152, and the common iliac arteries 154 and 156 and their respective branches are anterior to, and generally co-linear with, the spinal column 128 as shown in FIG. 5. Accordingly, when using the Pararectal Retroperitoneal Approach, at least some of these blood vessels must be moved to the side to expose the targeted area of the spinal column 128. During an index surgical procedure, movement of the blood vessels is accomplished by retracting the vena cava 146 and the abdominal aorta 152 to one side to expose the lumbar L4 138 and lumbar L5 140 vertebrae or by spreading the common iliac vein 148 and the common iliac artery 154 apart from the common iliac vein 150 and the common iliac artery 156 to expose the area about the lumbar L5 140 and the sacrum 142. Depending on the actual location of the veins and arteries of a particular patient and the area being targeted, branches of the iliac vessels may need to be moved in addition to or in place of the iliac vessels.

The blood vessels and surrounding tissue exhibit sufficient flexibility and looseness for the amount of retraction required to access areas using the Pararectal Retroperitoneal Approach during an initial surgery on a target area. After the initial surgery, however, scar tissue and/or adhesions may form about the surgical path and restrict the flexibility and looseness of the anatomical parts around the path to and in the area of the target area. To facilitate a revision surgery in the same area as the index surgery, a protective pad may be used to reduce complications resulting from scar tissue and/or adhesions. Preferably, the protective pad is attached to the spinal column 128 during the initial surgical operation. More preferably, the protective pad is attached after a procedure has been conducted on a target area and before the blood vessels or other anatomical parts are released from a retracted position.

FIG. 6 depicts a portion of the prevertebral space 144 after the blood vessels have been released from retraction. The protective pad 158 is attached to the lumbar L4 138 vertebra with two fasteners 160 and 162 which are inserted through the fastener areas 164 and 166, respectively. Preferably, holes are provided in the fastener areas 164 and 166 which allow the shafts (not shown) of the bone fasteners 160 and 162, which in this embodiment are screws, to pass through the protective pad 158. Similarly, the protective pad 158 is attached to the lumbar L5 140 vertebra with two fasteners 168 and 170 which are inserted through the fastener areas 172 and 174, respectively.

In this configuration, the base 176 of the protective pad 158 is located adjacent to the spinal column 128 and an overlying portion 178 and a fluid pocket 180 are located beneath the vena cava 146 and the abdominal aorta 152 of the patient as shown in FIG. 7. In a preferred embodiment, the protective pad 158 is selected from a kit of protective pads having different sizes. This allows a pad to be selected with a length that extends, in this example, from about the mid-point of the lumbar L4 138 vertebra to about the mid-point of the lumbar L5 140 vertebra. Additionally, the width of the protective pad 158 is selected to ensure the fluid pocket 180 extends outwardly from the vena cava 146 and the abdominal aorta 152 on at least one side as is discussed more fully below. In this embodiment, FIG. 7 shows that the fluid pocket 180 extends outwardly from both the vena cava 146 and the abdominal aorta 152 in a medial-lateral direction. The overall width of the protective pad 158 is preferably selected to provide complete coverage of the targeted vertebrae from psoas to psoas.

The telltale 182 extends away from the protective pad 158 and includes a marker 184 which may be similar to the marker 126 of FIG. 1. To aid in rapidly locating the telltale 182 during a revision surgery, the end portion with the marker 184 may conveniently be tacked to the rectus of the patient or affixed to another readily identifiable location by some other means.

Accordingly, during a revision surgery on or near the targeted area of the first procedure, radiography is used to identify the location of the marker 184 on the telltale 182. Then, after preparing the incision area in accordance with a proper surgical protocol, an incision in the skin of the patient is made and the telltale 182 is located based upon the radiography. In this embodiment, the telltale 182 is shown attached to the base 176. Alternatively, the telltale 182 may be attached to the overlying portion 178. In the event the telltale 182 does not interfere with the remaining steps of the surgical procedure, the telltale 182 may remain attached to the patient. Alternatively, if the telltale 182 is attached to the overlying portion 178 or will interfere with ensuing steps, the telltale 182 is detached from the patient.

In either event, the surgeon then follows the telltale 182 to the protective pad 158. After lysis of adhesions on the portion of the pad 158 on the side opposite the direction of desired retraction, a longitudinal incision 186 is made through the overlying portion 178 along a line adjacent to the vena cava 146 or the abdominal aorta 152 as shown in FIG. 8. The width of the fluid pocket 180 preferably extends outwardly of both the vena cava 146 and the abdominal aorta 152. This allows a surgeon to select the direction in which the blood vessels will be retracted based upon the particular condition of the patient. If the fluid pocket only extends outwardly of one of the two blood vessels, then the incision is preferably made to allow retraction of the blood vessels in a direction opposite the direction in which the fluid pocket extends outwardly of the one of the two blood vessels.

The overlying portion 178 may then be manipulated to retract the adjacent blood vessel away from the longitudinal incision 186 allowing a transverse incision 188 to be made in the overlying portion 178 at one end of the protective pad 158 and another transverse incision 190 along the opposite end of the protective pad 158. The longitudinal incision 186 and the transverse incisions 188 and 190 form a leaf 192.

Once the leaf 192 is sufficiently formed, a retractor is placed through the longitudinal incision 186 and into the fluid pocket 180. The retractor is used to move the leaf 192 in a direction away from the longitudinal incision 186. If needed, any of the incisions may be further extended during retraction. As shown in FIG. 9, the leaf 192, acting as a protective layer, is used to retract the vena cava 146 and the abdominal aorta 152 to reveal an exposed portion 194 of the base 176. An incision may then be made through the exposed portion 194 to reveal the targeted area.

As stated above, when using the Pararectal Retroperitoneal Approach in the area about the lumbar L5 140 and the sacrum 142, the common iliac vein 148 and the common iliac artery 154 are spread apart from the common iliac vein 150 and the common iliac artery 156. Accordingly, it is desirable to form two different leaves from the protective pad, one leaf for each set of blood vessels. The protective pad 158 may be used in this setting with appropriate modification of the location of the longitudinal cut to a central area and using transverse cuts to from two leaves. An alternative protective pad that may be used is the protective pad 200 shown in FIG. 10.

The protective pad 200 has a generally rectangular base 202 with four fastener holes 204, 206 208 and 210 located at each of the four corners. An overlying portion 212 is attached to the base 202 so as to define a fluid pocket 214 (see FIG. 11). The overlying portion 212 may be attached to the base 202 by use of an adherent or other acceptable method such as ultrasonic welding. The fluid pocket 214 is generally plough shaped with a narrow end portion 216. Two trailing portions 218 and 220 extend away from the end portion 224 and diverge from each other. The trailing portions 218 and 220 join a wide end portion 222 so as to form a generally triangular shape when viewed from above the fluid pocket 214 (see FIG. 12). The protective pad 200 further includes a telltale 224 which in this embodiment extends from the narrow end portion 216. The telltale 224 includes a marker 226.

The protective pad 200 is implanted on a bone such as the spinal column 128 following essentially the same steps set forth above with respect to the protective pad 158. The procedure for performing a revision surgery in the vicinity of the implanted protective pad 200 is the same as the method set forth above with respect to protective pad 158 until the telltale 224 is followed to the protective pad 200.

Figure 14:
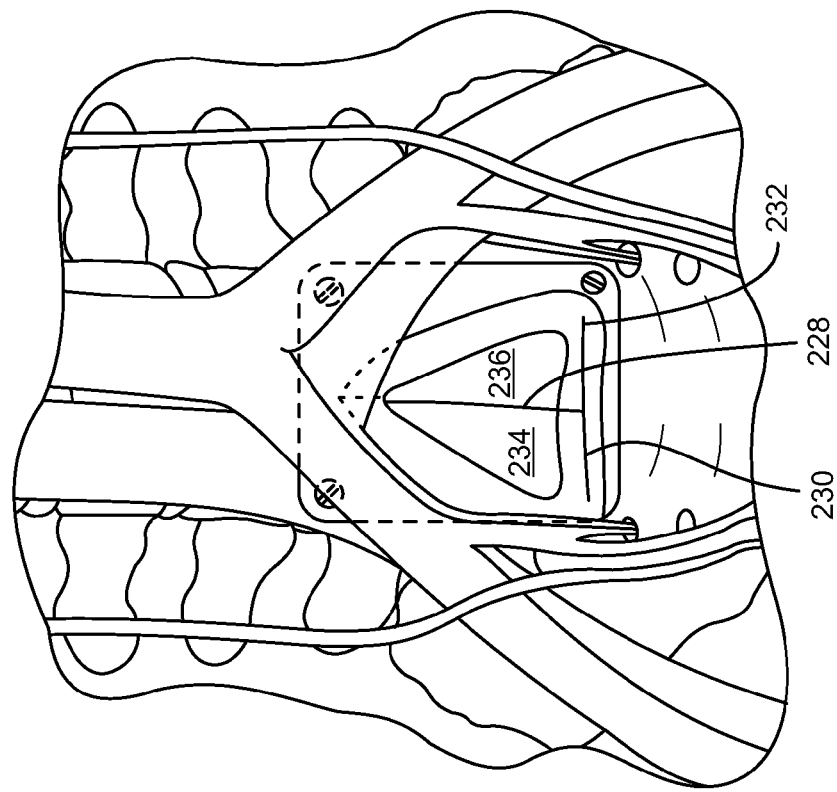
FIG. 14 shows a partial anterior perspective view of the protective pad of FIG. 10 located on a patient with incisions made in the overlying portion of the protective pad to form a leaf.
Figure 13:
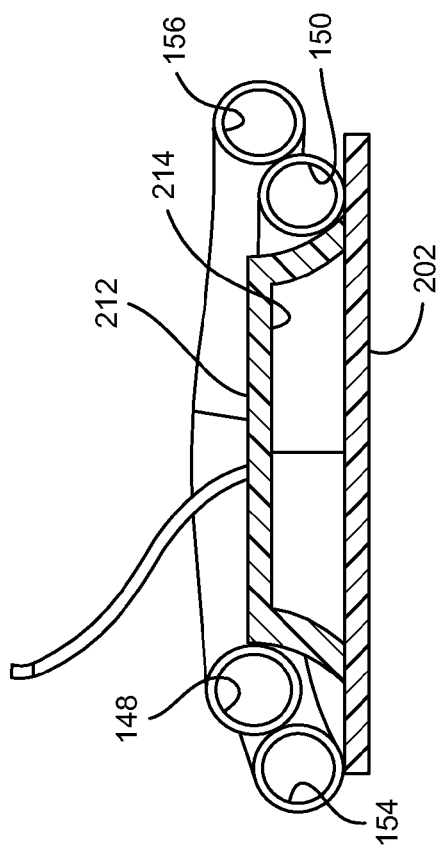
FIG. 13 shows a cross-sectional view of the protective pad of FIG. 10 taken along the line C-C of FIG. 10 in position between the common ileac arteries and veins of the patient.

The protective pad 200 is configured such that when it is implanted in the area of the lumbar L5 140 and the sacrum 142, the common iliac vein 148 and the common iliac artery 154 are spaced apart from the common iliac vein 150 and the common iliac artery 156 by the plough shaped fluid pocket 214 as shown in FIG. 13. The protective pad 200 is further configured such that the overlying portion 212 extends away from the spinal column 128 to about the same height as the aorta is located above the spinal column 128. Accordingly, when the telltale 224 is tracked to the protective pad 200, at least some of the overlying portion 212 will be exposed between the iliac vein 148 and the common iliac artery 154 on one side and the common iliac vein 150 and the common iliac artery 156 on the other side as shown in FIG. 14.

The area about the protective pad 200 is then prepared for retraction of the blood vessels. In a preferred approach, a longitudinal incision 228 is made through the overlying portion 212 along a line between the narrow end portion 216 and the wide end portion 222. Typically, the longitudinal incision 228 will be made approximately along the centerline of the overlying portion 212. Depending on the conditions for a particular patient, the location of the incision may be adjusted to one side or the other. Transverse incisions 230 and 232 are made along the wide end portion 222. Of course, the order of the incisions may be modified. The longitudinal incision 228 and the transverse incisions 230 and 232 form leafs 234 and 236.

Figure 15:
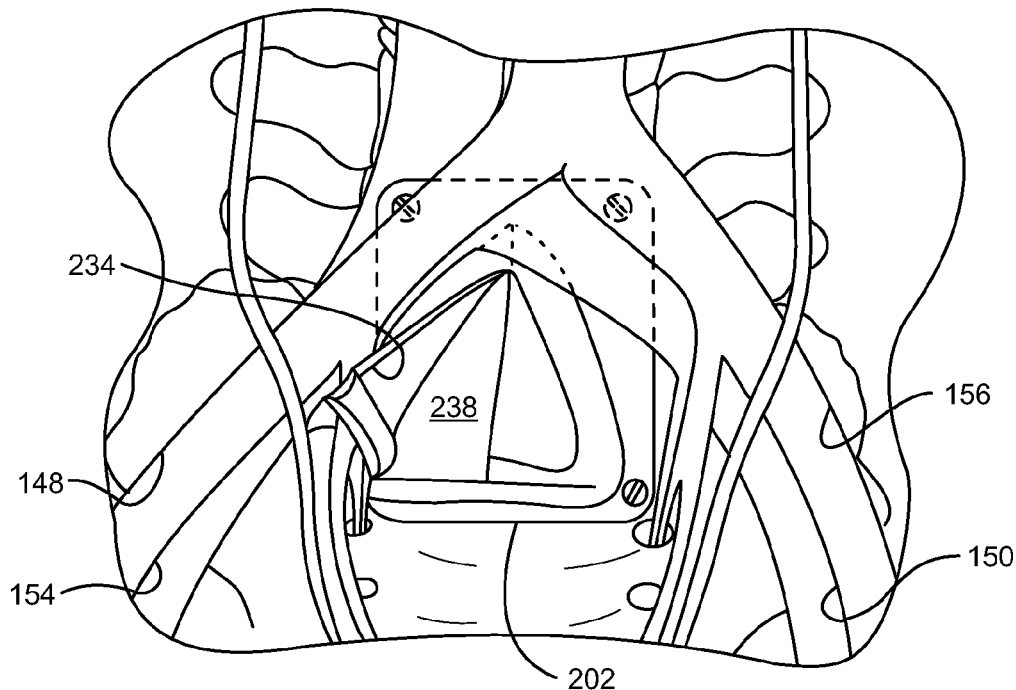
FIG. 15 shows a partial anterior perspective view of the protective pad of FIG. 14 with one leaf retracted so as to retract one common ileac vein and one common ileac artery of the patient and to expose a portion of the base of the protective pad.

Once a leaf is sufficiently formed, a retractor (not shown) is placed through the longitudinal incision 228 and into the fluid pocket 214. The retractor is used to move one of the leafs 234 or 236 in a direction away from the longitudinal incision 228. As shown in FIG. 15, the leaf 234 is positioned against the common iliac vein 148 and the common iliac artery 154 and their branches. The leaf 234 thus provides protection to the common iliac vein 148, the common iliac artery 154 and their respective branches. The leaf 234 may further be used to retract the common iliac vein 148 and the common iliac artery 154 and their branches to reveal exposed portion 238 of the base 202.

Figure 16:
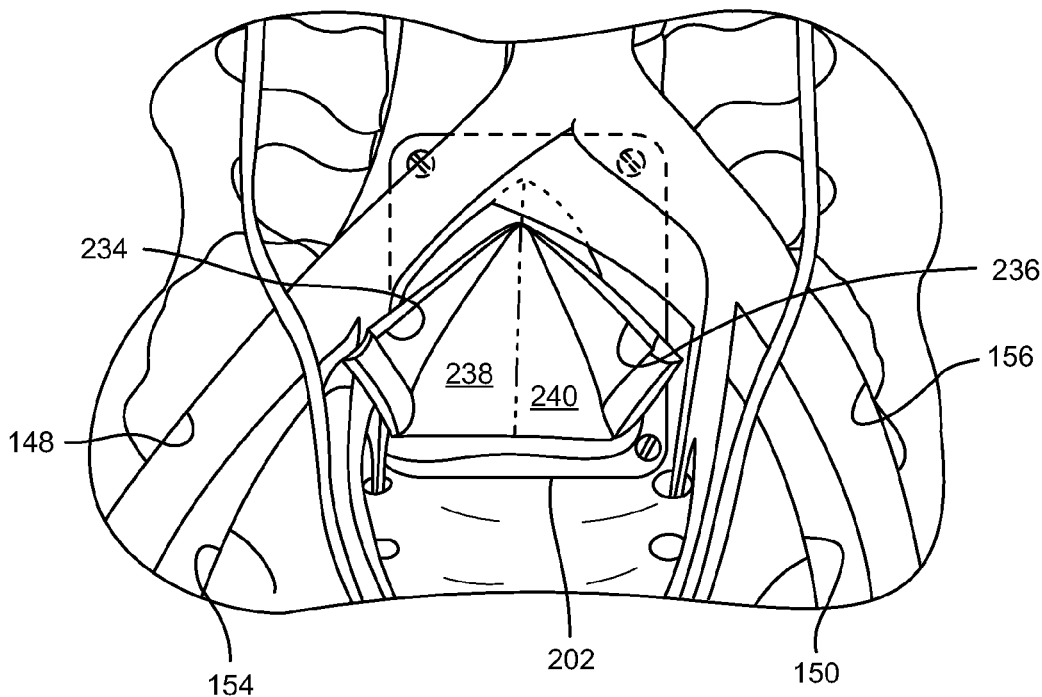
FIG. 16 shows a partial anterior perspective view of the protective pad of FIG. 14 with two leafs retracted so as to retract both common ileac veins and both common ileac arteries of the patient and to expose two portions of the base of the protective pad.

If desired, a second retractor (not shown) may be used to move the other of the leafs 234 or 236 in a direction opposite of the direction of the first retraction. Thus, as shown in FIG. 16, the leaf 236 is positioned against the common iliac vein 150 and the common iliac artery 156 and their branches. The leaf 236 thus provides protection to the common iliac vein 150, the common iliac artery 156 and their respective branches. The leaf 234 may further be used to retract the common iliac vein 150 and the common iliac artery 156 and their branches to reveal portion 240 of the base 202. An incision may then be made through the base 202 using one or both of the exposed areas 238 and 240 to reveal the targeted area.

While the present invention has been illustrated by the description of exemplary processes and system components, and while the various processes and components have been described in considerable detail, applicant does not intend to restrict or in any way limit the scope of the appended claims to such detail. Additional advantages and modifications will also readily appear to those ordinarily skilled in the art. The invention in its broadest aspects is therefore not limited to the specific details, implementations, or illustrative examples shown and described. Accordingly, departures may be made from such details without departing from the spirit or scope of applicant's general inventive concept.

I claim:

1. A protective system for facilitating revision surgery comprising:
    a protective pad having a base portion and a retraction portion, the protective pad including at least one fastener hole structure defining at least one fastener hole; and
    at least one bone anchor configured to cooperate with the at least one fastener hole structure to affix the protective pad to a bone,
    wherein (i) the base portion defines a first internal surface, and (ii) the retraction portion defines a second internal surface,
    wherein the protective pad is configured to be moved from a first configuration to a second configuration,
    wherein, when the protective pad is in the first configuration, the retraction portion is located in relation to the base portion at a first relative position in which the retraction portion overlays the base portion to define at least part of a fluid pocket between the first internal surface and the second internal surface,
    wherein, when the protective pad is in the second configuration, the retraction portion is located in relation to the base portion at a second relative position in which the retraction portion is retracted away from the base portion so as to expose the first internal surface,
    wherein the fluid pocket is sealed such that fluid is not allowed to flow into or out of the fluid pocket.

2. The protective system of claim 1, wherein the fluid pocket contains a biologically inert gaseous fluid.

3. The protective system of claim 2, wherein the gaseous fluid is carbon dioxide.

4. The protective system of claim 1, further comprising:
    a telltale extending from the protective pad.

5. The protective system of claim 4, wherein the telltale comprises a radio dense material.

6. The protective system of claim 1, wherein the fluid pocket comprises:
    an end portion;
    a first trailing portion extending from the end portion; and
    a second trailing portion extending from the end portion and diverging from the first trailing portion.

7. The protective system of claim 1, wherein:
    when the protective pad is in the first configuration, the second internal surface of the retraction portion faces toward the first internal surface of the base, and
    when the protective pad is in the second configuration, at least a portion of the second internal surface of the retraction portion faces away from the first internal surface of the base.

8. The protective system of claim 1, wherein both the retraction portion and the base portion are formed from a flexible biocompatible material.

9. The protective system of claim 1, wherein the retraction portion and the base portion are both formed from an organosiloxane polymer material.

* * * * *